US00PP15990P3

(12) United States Plant Patent
Bakker

(10) Patent No.: US PP15,990 P3
(45) Date of Patent: Sep. 20, 2005

(54) LILAC PLANT NAMED 'GOLDEN ECLIPSE'

(50) Latin Name: *Syringa reticulata*
Varietal Denomination: Golden Eclipse

(75) Inventor: Robert Bakker, St. Catharines (CA)

(73) Assignee: J. C. Bakker & Sons Limited, St. Catharines (CA)

( * ) Notice: Subject to any disclaimer, the term of this patent is extended or adjusted under 35 U.S.C. 154(b) by 221 days.

(21) Appl. No.: 10/420,824

(22) Filed: Apr. 23, 2003

(65) Prior Publication Data

US 2004/0006801 P1 Jan. 8, 2004

(51) Int. Cl.[7] ..... A01H 5/00
(52) U.S. Cl. ..... Plt./248
(58) Field of Search ..... Plt./248

(56) References Cited

PUBLICATIONS

GTITM UPOV ROM Citation for 'Golden Eclipse' as per CA PBR 01–2536; Feb. 26, 2001.*
Canadian Plant Varieties Journal, No. 46, p. 96, Jan. 2003 (Published Feb. 17, 2003).
2000–2001 Catalog, p. 12, J.C. Bakker & Sons, Ltd., St. Catharines, Ontario, Canada.
2002–2003 Catalog, p. 18, J.C. Bakker & Sons, Ltd., St. Catharines, Ontario, Canada.

* cited by examiner

*Primary Examiner*—Kent L. Bell
(74) *Attorney, Agent, or Firm*—Burns, Doane, Swecker & Mathis, L.L.P.

(57) ABSTRACT

A new and distinct highly ornamental cultivar of *Syringa reticulata* Japanese Tree Lilac is provided. The Lilac plant has an upright compact growth habit. The foliage possesses variegation that initially is green with an irregular darker green center wherein the margins turn to a stable bright yellow-gold coloration upon maturity. The blossoms are white and are displayed during late spring to early summer. Good winter hardiness is made possible and the plant has been found to be free of insect and disease problems. The plant is particularly well-suited for providing distinctive ornamentation in the landscape.

3 Drawing Sheets

Figure 1:
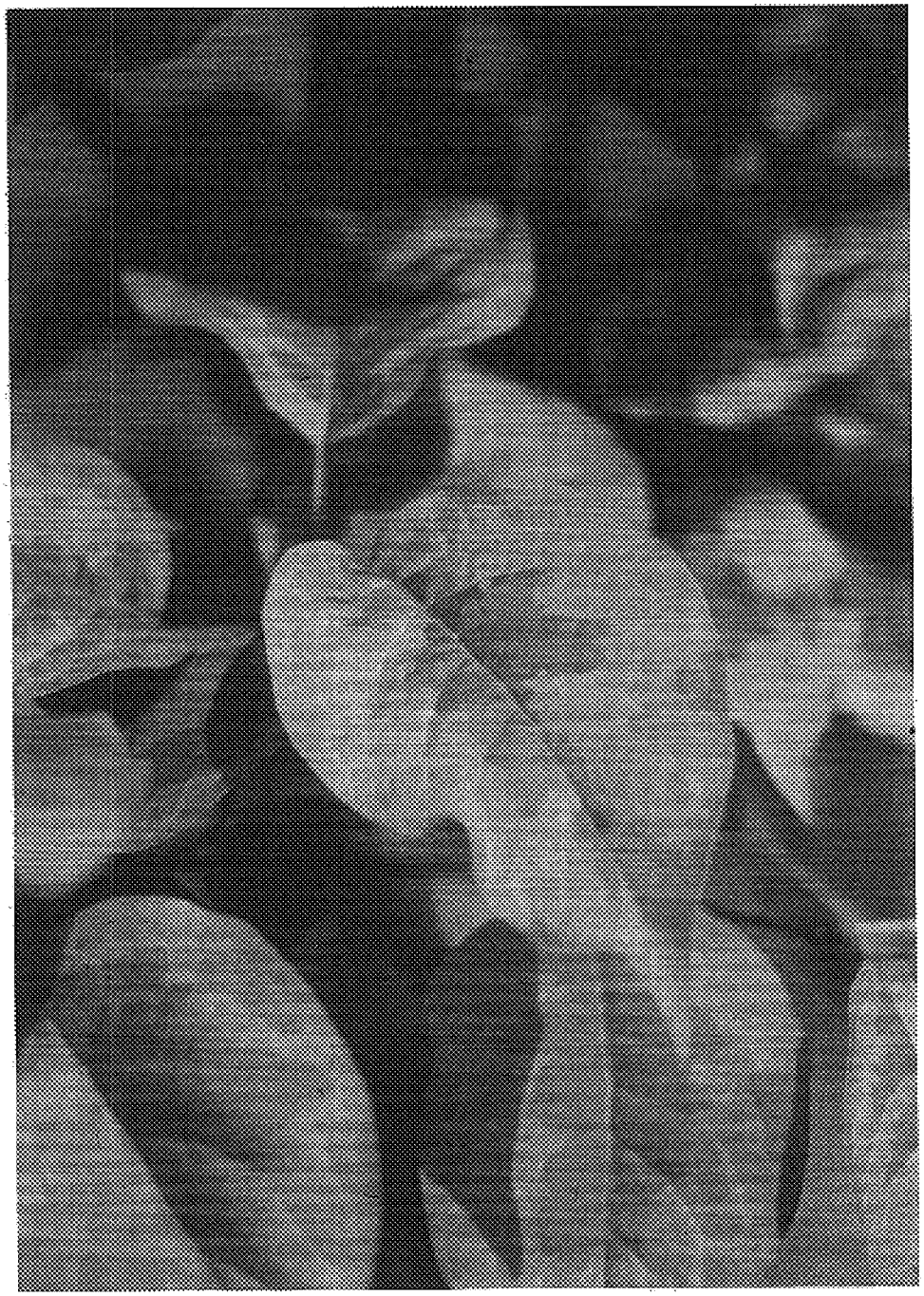

Botanical commercial classification: *Syringa reticulata*/ Lilac Plant.
Varietal denomination: cv 'Golden Eclipse'.

SUMMARY OF THE INVENTION

The new Lilac plant of the present invention was discovered during 1995 in a nursery setting at St. Catharines, Ontario, Canada, while growing within a large block of *Syringa reticulata* seedlings (unnamed and non-patented in the United States). The new variety was primarily selected because of the distinctive appearance of the foliage and is believed to be a whole plant mutation of unknown causation. Had the new variety not been discovered and preserved, it would have been lost to mankind.

It was found that the cultivar of *Syringa reticulata* exhibits the following combination of characteristics:

(a) exhibits an upright compact growth habit,
(b) forms attractive variegated foliage that initially is green with an irregular darker green center wherein the margins turn to a stable bright yellow-gold coloration upon maturity,
(c) forms fragrant white flowers in late spring to early summer,
(d) is relatively free of insect and disease problems, and
(e) is well-suited for providing distinctive ornamentation in the landscape.

The stability of the variegated foliage has been well confirmed during observations to date. Such coloration also has displayed excellent resistance to sunburn.

The new cultivar of the present invention can be readily distinguished from the parental plant and the 'Ivory Silk' cultivar (non-patented in the United States). The parental *Syrina reticulata* lacks the variegated foliage possessed by the new cultivar, possesses a slightly thicker branch and trunk caliper than the new cultivar, possesses more glossiness on the upper leaf surface than the new cultivar, possesses less reddish brown coloration on a one year-old shoot than the new cultivar, and possesses a slightly wider and longer leaf blade than the new cultivar. Also, the 'Ivory Silk' cultivar lacks variegated foliage, displays less anthocyanin coloration on one year-old shoots, and forms larger flowers.

The new cultivar of the present invention has been asexually propagated beginning in 1996 and each year thereafter at St. Catharines, Ontario, Canada, by summer budding on *Syringa reticulata* (unnamed and non-patented) rootstock. The distinctive characteristics of the new cultivar including the variegated appearance of the foliage have been found to be stable and to be capable of transmission from one generation to another following such asexual propagation. The new variety reproduces true to type in successive generations of asexual reproduction.

The new cultivar of the present invention has been named 'Golden Eclipse'.

BRIEF DESCRIPTION OF THE PHOTOGRAPHS

The accompanying photographs show, as true as is reasonably possible to make the same in color illustrations of this character, the distinctive foliage of the new cultivar. The plants were propagated by summer budding on *Syringa reticulata* (unnamed and non-patented) understock and were growing in the field at St. Paul, Minn.; U.S.A.

FIG. 1—shows the new green foliage as it emerges in the springtime. The darker green irregular central area of the leaves is apparent. The illustrated plant was approximately three years of age.

Figure 2:
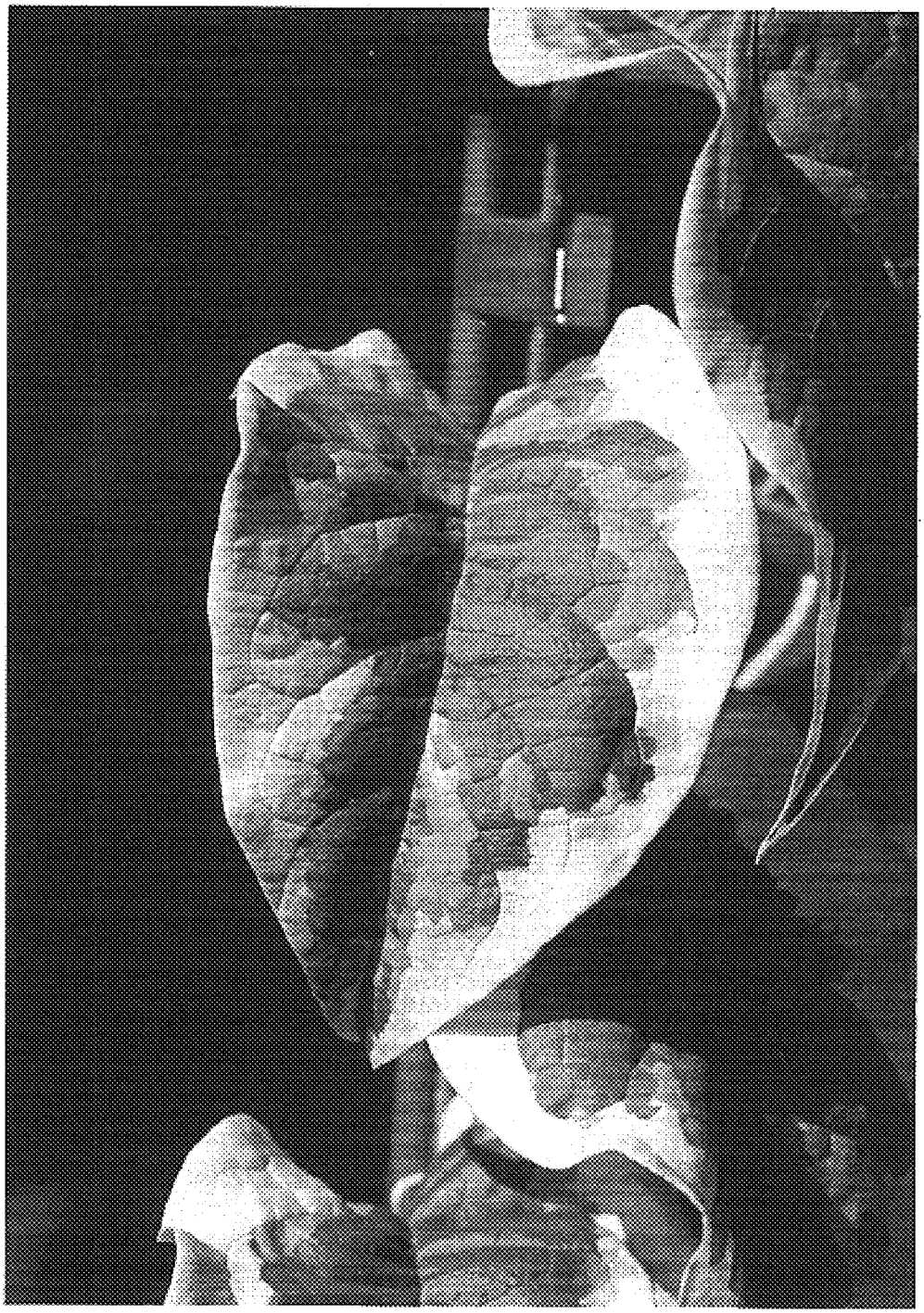

FIG. 2—shows a closer view of typical leaves during the summer. The margins of the leaves have turned to bright yellow-gold, and the irregular dark green area in the center of the leaves gives the illusion of an eclipse. The illustrated plant was approximately three years of age and was tied to a pole for added support during the early years of its growth. As the tree matures, such support can be removed.

Figure 3:
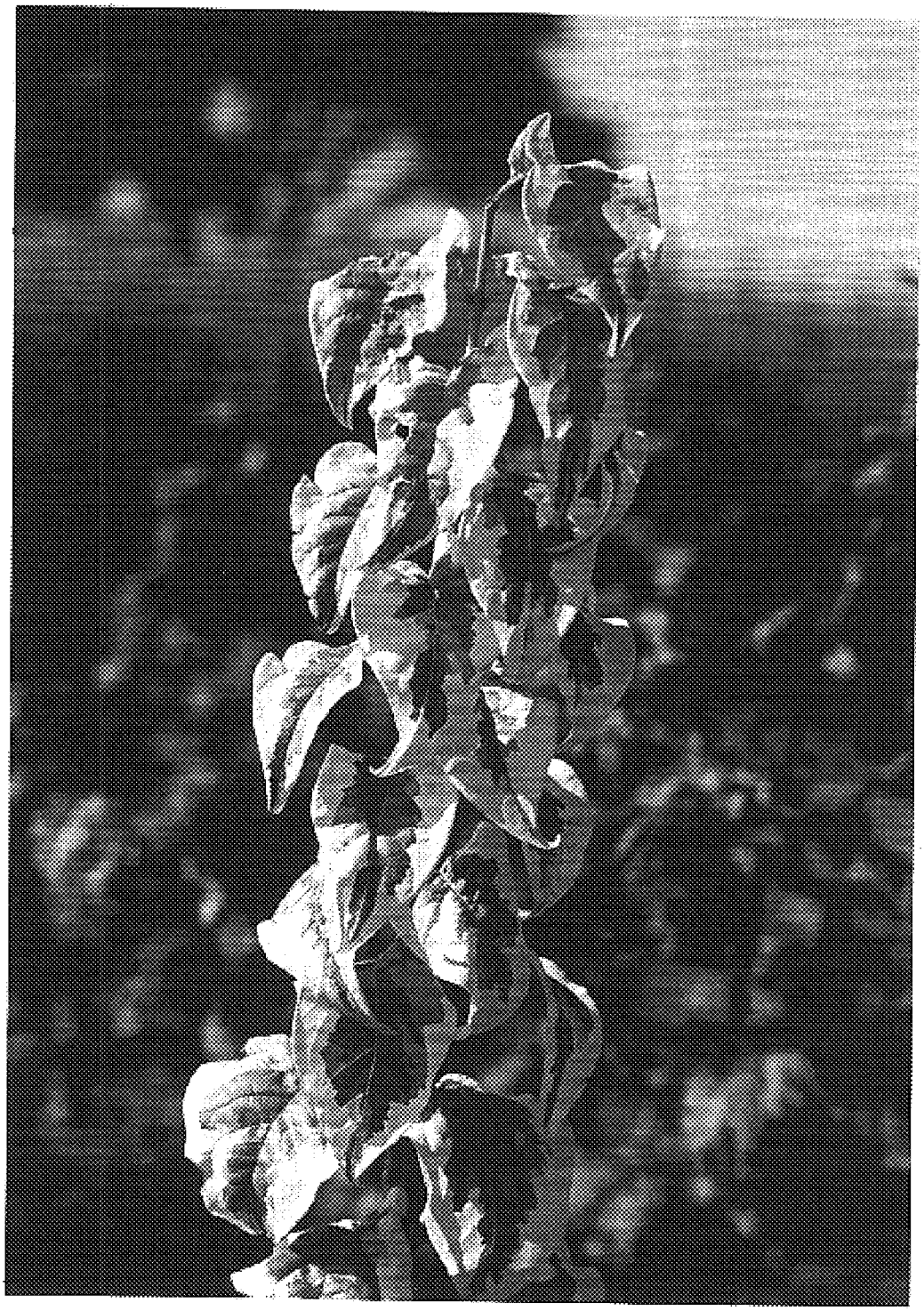

FIG. 3—shows the top portion of a typical tree bearing the distinctive variegated foliage during the summer. The tree displays a straight trunk and short branches, and was approximately two years of age.

DETAILED DESCRIPTION

The chart used in the identification of colors is The R.H.S. Colour Chart of The Royal Horticultural Society, London, England. Common terms are to be accorded their ordinary dictionary significance. The description is based upon the observation of two and three year-old plants that were summer budded on *Syringa reticulata* (unnamed and non-patented) understock and were growing in the field at St. Catharines, Ontario, Canada.

Botanical classification: *Syringa reticulata*, cv. 'Golden Eclipse'. The parental plant was unnamed and non-patented in the United States.

Plant:

*Growth habit.*—Upright, compact, and bushy.

*Size.*—A two year-old tree commonly displays a height of approximately 1.25 to 2 m and a diameter of approximately 0.5 to 1 m. A four year-old tree commonly displays a height of approximately 2.5 to 3 m and a diameter of approximately 1 to 1.5 m.

*Density of crown.*—Medium.

*Growth rate.*—Similar to other Lilacs.

Stem characteristics:

*Color.*—On a young shoot the coloration changes from green (Yellow-Green Group 144A and 144B) to Greyed-Orange Group 176A, 176B and 176C and between Greyed-Red Group 178A and 178B with anthocyanin coloration of medium intensity (Greyed-Red Group 178A and 178B). Such anthocyanin coloration is considerably stronger than that of the 'Ivory Silk' cultivar.

*Size.*—Commonly approximately 15 to 20 cm in length and approximately 3 mm in diameter when measured 2 cm from the tip.

*Internode length.*—Commonly approximately 3 to 5 cm.

*Lenticels.*—Commonly approximately 44 to 76 (average approximately 62) between nodes on one year-old shoots on the sunny side.

*Pubescence.*—Very sparse on a one year-old shoot.

*Vegetative bud.*—Bears no or very sparse pubescence.

Bark:

*Color.*—On a one year-old shoot the bark is reddish-brown on the sunny side. This compares to a greenish-grey coloration for the 'Ivory Silk' cultivar.

Foliage:

*Leaf shape.*—Ovate.

*Form.*—Simple.

*Leaf apex.*—Acute.

*Leaf base.*—Rounded.

*Leaf margins.*—Entire with weak undulation.

*Cross-section.*—Slightly convex.

*Pubescence.*—None.

*Upper surface.*—Medium glossiness.

*Glaucosity.*—Absent.

*Texture.*—Leathery.

*Length.*—Approximately 18 to 21 cm (mean 19 cm). This can be compared to approximately 15 to 18 cm (mean 17 cm) for the 'Ivory Silk' cultivar. The leaves tend to be larger on very young trees.

*Width.*—Approximately 11 to 12 cm (mean 11.5 cm). This can be compared to approximately 12 cm for the 'Ivory Silk' cultivar. The leaves tend to be larger on very young trees.

*Color.*—The leaf blade is variegated while that of the 'Ivory Silk' cultivar has no variegation. As shown in FIG. 1 initially the leaves are green (near Yellow-Green Group 144A and 144B) with an irregular darker green central area (near Green Group 131A). As the leaves mature during the summer, the variegated appearance becomes more apparent with the leaf margins assuming a bright yellow-gold appearance near Yellow-Green Group 154A, 154B and 154C and the irregular dark green near Green Group 131A central area gives an illusion of an eclipse. The variegation can be seen through the underside of a leaf. The foliage has been found to hold its coloration well even in full sun. Also, the foliage well resists sunburn. The fall foliage coloration is insignificant.

*Petioles.*—Commonly approximately 1.25 cm in length, approximately 2.2 to 2.6 mm in diameter, and near Yellow-Green Group 143C and 144C in coloration.

Inflorescence:

*Arrangement.*—In semi-erect panicles and mainly from terminal buds as the 'Ivory Silk'cultivar.

*Buds.*—Yellow-White Group 158C in coloration when unopened. This compares to Yellow-White Group 158D for the 'Ivory Silk' cultivar. A dormant bud commonly is ovoid in configuration with the outermost scale centered directly over the leaf scar. Dormant buds commonly are approximately 4 to 5 mm in length and approximately 3 to 4 mm in diameter.

*Flower configuration.*—Very short funnel-shaped corolla tubes with four flat to reflexed rounded corolla lobes. The lobes are flat to reflexed in cross section when the flower is open, approximately 2.75 mm in length, and possess an entire margin.

*Flower size.*—Approximately 4 to 6 mm (5 mm mean) in diameter. This compares to approximately 7.9 mm (8 mm mean) for the 'Ivory Silk' cultivar. The depth of the corolla tube commonly is approximately 5 to 8 mm.

*Flower color.*—When ⅔ open, the coloration is White Group 155B. This can be compared to White Group 155D when ⅔ open for the 'Ivory Silk' cultivar. When fully open, the upper side of the corolla lobes is White Group 155D. This can be compared to lighter than White Group 155D for the 'Ivory Silk' cultivar. The outer surface of the corolla tube is Yellow-White Group 158D. The outside surface of the corolla lobes is White Group 155D and the inside surface of the corolla lobes is slightly lighter than White Group 155D.

*Stamens*.—Two in number and approximately the same length as the corolla tube.

*Anthers*.—White in coloration.

*Pollen*.—Sparse and Yellow Group 11B in coloration.

*Pistil*.—One in number.

*Style*.—Commonly approximately 2.0 mm in length and White Group 155D in coloration.

*Stigma*.—Commonly approximately 0.1 to 0.2 mm in size and near White Group 155B in coloration.

*Fragrance*.—Medium intensity.

*Flowering time*.—Late spring to early summer, and commenced on June $20^{th}$ in 2002. Flowers commonly are absent on one and two year-old trees.

Hardiness: Can be grown in U.S.D.A. Hardiness Zone No. 4.

Culture: Similar to the 'Ivory Silk' cultivar.

Vegetation: Vigorous.

Disease/pest resistance: Has proven to be very disease and pest resistant during observations to date. No pesticide applications have been needed.

Landscape usage: Provides a hardy highly distinctive fragrant tree having a distinctive foliage coloration that can be grown as a specimen plant to provide attractive ornamentation in the landscape.

I claim:

1. A new and distinct *Syringa reticulata* plant having the following combination of characteristics:

(a) exhibitis upright compact growth habit, (b) forms attractive variegated foliage that initially is green with an irregular darker green center wherein the margins turn to a stable bright yellow-gold coloration upon maturity, (c) forms fragrant white flowers in the late spring to early summer, (d) is relatively free of insect and disease problems, and (e) is well-suited for providing distinctive ornamentation in the landscape;

substantially as illustrated and described.

* * * * *